US010959707B2

(12) United States Patent
Weber

(10) Patent No.: US 10,959,707 B2
(45) Date of Patent: Mar. 30, 2021

(54) METHOD FOR OBTAINING A SALIVA SAMPLE AND COLLECTING DEVICE

(71) Applicant: BOEHRINGER INGELHEIM VETMEDICA GmbH, Ingelheim am Rhein (DE)

(72) Inventor: Christoph Weber, Ingelheim am Rhein (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 413 days.

(21) Appl. No.: 15/576,475

(22) PCT Filed: Jun. 8, 2016

(86) PCT No.: PCT/EP2016/025056
§ 371 (c)(1),
(2) Date: Nov. 22, 2017

(87) PCT Pub. No.: WO2016/198168
PCT Pub. Date: Dec. 15, 2016

(65) Prior Publication Data
US 2018/0153523 A1    Jun. 7, 2018

(30) Foreign Application Priority Data
Jun. 8, 2015    (DE) ..................... 10 2015 007 097.5

(51) Int. Cl.
*A61B 10/00*    (2006.01)
*A01K 29/00*    (2006.01)
(Continued)

(52) U.S. Cl.
CPC .......... *A61B 10/0051* (2013.01); *A01K 29/00* (2013.01); *A61B 42/10* (2016.02); *A61B 50/30* (2016.02); *A61J 1/2086* (2015.05); *A61J 19/00* (2013.01); *A61B 10/0096* (2013.01); *A61B 2050/3008* (2016.02); *A61B 2503/40* (2013.01)

(58) Field of Classification Search
CPC .................................................. A61B 10/0051
See application file for complete search history.

(56) References Cited

U.S. PATENT DOCUMENTS 3,521,754 A    7/1970 Ireland
5,196,001 A    3/1993 Kao
(Continued)

FOREIGN PATENT DOCUMENTS

CN    201275091 Y    7/2009
CN    202776387 U    3/2013
(Continued)

*Primary Examiner* — Puya Agahi
(74) *Attorney, Agent, or Firm* — David S. Safran; Roberts Calderon Safran & Cole, P.C.

(57) ABSTRACT

A method for obtaining a saliva sample from an animal, particularly a pig, by means of a receiving device and a collecting device with an integrated filter, and a method of using a collecting device with an integrated filter for obtaining a saliva sample from an animal, particularly a pig. In addition, a collecting device comprising a bag, a removable container and a filter, and a kit having such a collecting device, and a receiving device for taking saliva from an animal, particularly a pig.

9 Claims, 4 Drawing Sheets

(51) Int. Cl.
*A61J 1/20* (2006.01)
*A61B 42/10* (2016.01)
*A61B 50/30* (2016.01)
*A61J 19/00* (2006.01)

(56) References Cited

U.S. PATENT DOCUMENTS

| | | | | |
|---|---|---|---|---|
| 5,260,031 A | * | 11/1993 | Seymour | A61B 5/411 |
| | | | | 422/419 |
| 5,268,148 A | * | 12/1993 | Seymour | A61B 10/0051 |
| | | | | 422/401 |
| 5,910,122 A | | 6/1999 | D'Angelo | |
| 7,387,899 B1 | * | 6/2008 | D'Angelo | A61B 10/0051 |
| | | | | 422/500 |
| 2002/0197738 A1 | | 12/2002 | Matsumoto et al. | |
| 2003/0082528 A1 | | 5/2003 | Smith et al. | |
| 2007/0062460 A1 | | 3/2007 | Simer | |
| 2011/0008771 A1 | | 1/2011 | Hanselle et al. | |

FOREIGN PATENT DOCUMENTS

| | | | |
|---|---|---|---|
| CN | 103543036 A | | 1/2014 |
| CN | 203369923 U | | 1/2014 |
| CN | 103558058 A | | 2/2014 |
| CN | 203502260 U | | 3/2014 |
| CN | 203700242 U | | 7/2014 |
| CN | 104546017 A | | 4/2015 |
| DE | 7436286 U | | 7/1975 |
| DE | 29801590 U1 | | 4/1998 |
| JP | 3187250 U | * | 11/2013 |
| WO | 95/30484 A1 | | 11/1995 |

* cited by examiner

METHOD FOR OBTAINING A SALIVA SAMPLE AND COLLECTING DEVICE

BACKGROUND OF THE INVENTION

Field of the Invention

The present invention relates to a method for obtaining a saliva sample from an animal, particularly a pig wherein saliva from the animal is absorbed by a receiving device in a collecting device comprising a bag and at least one container device for obtaining a filtered saliva sample from an animal, such as a pig, the collecting device having a bag, a filter and at least one removable container, a kit for obtaining a filtered saliva sample from an animal, particularly a pig, and a method of using a collecting device with an integrated filter for obtaining a saliva sample from an animal, particularly a pig.

Saliva and/or liquid from the oral cavity of an animal contains, among other things, water, proteins, electrolytes, mucus, serum and serum components, blood cells, mucous membrane cells as well as microorganisms and antibodies.

For the veterinary examination of animals, particularly domesticated mammals such as pigs, cows, goats, sheep or the like, it is conventional to examine the saliva or oral cavity liquid of the animal for diseases and/or pathogens. Diseases and/or pathogens can be detected in particular by the detection of antibodies and/or microorganisms such as bacteria, viruses and/or fungi in the saliva of the affected animal.

Description of Related Art

The removal of saliva or oral cavity liquid from an animal, particularly a pig, or the taking of a sample for analysis or a saliva sample, is carried out for example as described in US 2003/0082528 A1 and US 2007/0062460 A1 using a receiving device such as a rope or cord. Preferably, the saliva is taken up or absorbed by the receiving device by oral contact between the animal and the receiving device, particularly by chewing and/or biting. Then the saliva or sample material taken is separated from the receiving device, for example by wringing out the receiving device. The saliva sample thus obtained is then subjected to examination by a veterinary specialist.

The above-mentioned method for obtaining a saliva sample from an animal has the disadvantage, however, that the quantity and/or quality of the saliva sample thus obtained is often inadequate for the subsequent veterinary examination. In addition to the contaminants already present in the saliva, the sample material taken may be further contaminated by the handling of the receiving device at the sampling site. This adversely affects the subsequent veterinary examination and/or requires complex processing of the resulting saliva sample in the laboratory.

Against this background, the present invention sets out to provide a method for obtaining a saliva sample from an animal, and an improved collecting device for separating sample material or saliva from a receiving device, preferably thereby achieving or assisting with a simple, safe, inexpensive, efficient, hygienic and/or fast method of taking a saliva sample, reducing contaminants or particles in the saliva sample and/or enabling the saliva sample obtained to be subjected to direct or immediate veterinary examination, preferably without any further processing.

SUMMARY OF THE INVENTION

The above problem is solved by methods, a collecting device, and a kit as described herein In the proposed method for obtaining a saliva sample from an animal, particularly a pig, saliva from the animal is taken up or absorbed by a receiving device, particularly a rope, preferably by oral contact with the animal. Preferably, the receiving device is then at least partially placed in an at least partially flexible, elastic, pliable and/or compressible collecting device or received by an at least partially flexible, elastic, pliable, deformable and/or compressible collecting device, and/or the saliva or sample material absorbed by the receiving device is separated from the receiving device inside the collecting device, preferably by compressing or deforming the collecting device.

By the term "sample material" is preferably meant, according to the present invention, the saliva taken from the animal during testing. Particularly preferably, the sample material is the saliva taken from the animal by means of the receiving device or the saliva absorbed by or adhering to the receiving device. The sample material preferably comprises saliva and/or consists predominantly of saliva. However, the sample material may also contain contaminants or particles such as fibers of the receiving device, food residues, dust, fecal traces or the like. Preferably, the sample material is the starting material for a saliva sample and/or the sample material is processed, particularly eluted, in order to obtain or prepare a saliva sample.

By the term "receiving device" is preferably meant, according to the present invention, a construction which is configured particularly to remove saliva from the animal, by preferably oral contact with an animal, particularly by chewing and/or biting of the receiving device, and/or for sucking up and/or absorbing saliva and/or sample material from the animal and/or for preparing a saliva sample. Particularly preferably, the receiving device is embodied as a rope, cord or the like.

In one aspect of the present invention, the animal's saliva absorbed by the receiving device or the sample material within the collecting device is at least partially filtered, the filtered saliva or the filtered sample material forming a saliva sample and/or being suitable as a saliva sample for veterinary examination. This makes it possible to work up the saliva or obtain a filtered saliva sample in a particularly simple, fast, hygienic and/or inexpensive manner.

Preferably, the saliva and particles or contaminants are separated from one another in the collecting device and/or by means of the collecting device and/or by—in particular, partial—deformation or compression of the collecting device, particularly so that filtered sample material or a filtered saliva sample is provided in the collecting device.

By the term "saliva sample" is preferably meant, according to the present invention, the processed, particularly eluted and/or filtered, sample material. In particular, the saliva sample can be analyzed and/or fed into an analyzer immediately or directly and/or without any further processing.

The proposed collecting device preferably comprises a bag and at least one removable container, the bag preferably being at least substantially flexible, elastic, compressible and/or deformable and the container being at least substantially rigid.

By the term "collecting device" is preferably meant, according to the present invention, a construction which is embodied in particular to at least temporarily store biological material and/or fluids such as saliva, keep them away from the environment and/or collect them. Particularly preferably, a collecting device according to the present invention is a container, a reservoir, a bag, a funnel and/or a vessel. Most particularly, in a collecting device according to the present invention, saliva or the sample material taken from the animal by means of the receiving device can be separated from the receiving device, particularly dissolved or eluted out of it, wrung out, squeezed out and/or removed by centrifuging.

According to a first aspect which can also be implemented independently, the collecting device comprises a filter and/or a filter is integrated in the collecting device. Particularly preferably, the container of the collecting device is fluidically connected to the bag via the filter. Such a construction enables particularly simple, fast and/or cheap filtration of the saliva or of the sample material, or the obtaining of a filtered saliva sample. In particular, using the proposed collecting device, the saliva or the sample material can be filtered at least substantially at the same time as and/or automatically with the separation of the saliva or sample material from the receiving device or the dissolving of the sample material out of the receiving device.

According to a second aspect which can also be implemented independently, the bag of the collecting device comprises a first section and a second section, the first section being fluidically connected to the second section through a filter and the container being fluidically connected to one of the sections. This results in corresponding advantages.

The proposed kit for obtaining a filtered saliva sample from an animal, particularly a pig, preferably comprises a receiving device, particularly a rope, for absorbing the saliva and a proposed collecting device. The kit optionally contains instructions for use, a pipette and/or a solvent for dissolving the saliva or sample material out of the receiving device. This results in corresponding advantages.

A kit in the sense of the present invention is, in particular, a combination and/or a system comprising the proposed receiving device and a collecting device. Preferably, the receiving device and the collecting device each form a component of the kit. The components of the kit are preferably sold in combination, particularly in a combined pack or the like. However, it is also possible for the above-mentioned components to be provided loose for using together. Preferably, a common or linking element is provided, such as, for example, instructions for use, handling recommendations or information in the text on one or more of the components of the kit or on the common packaging.

A proposed method of using a collecting device provides that saliva or sample material should be filtered by means of a filter integrated in the collecting device in order to obtain a filtered saliva sample. This results in corresponding advantages.

Additional advantages, features, properties and aspects of the present invention will become apparent from the following description of preferred embodiments with reference to the accompanying drawings

DETAILED DESCRIPTION OF THE INVENTION

Figure 1:
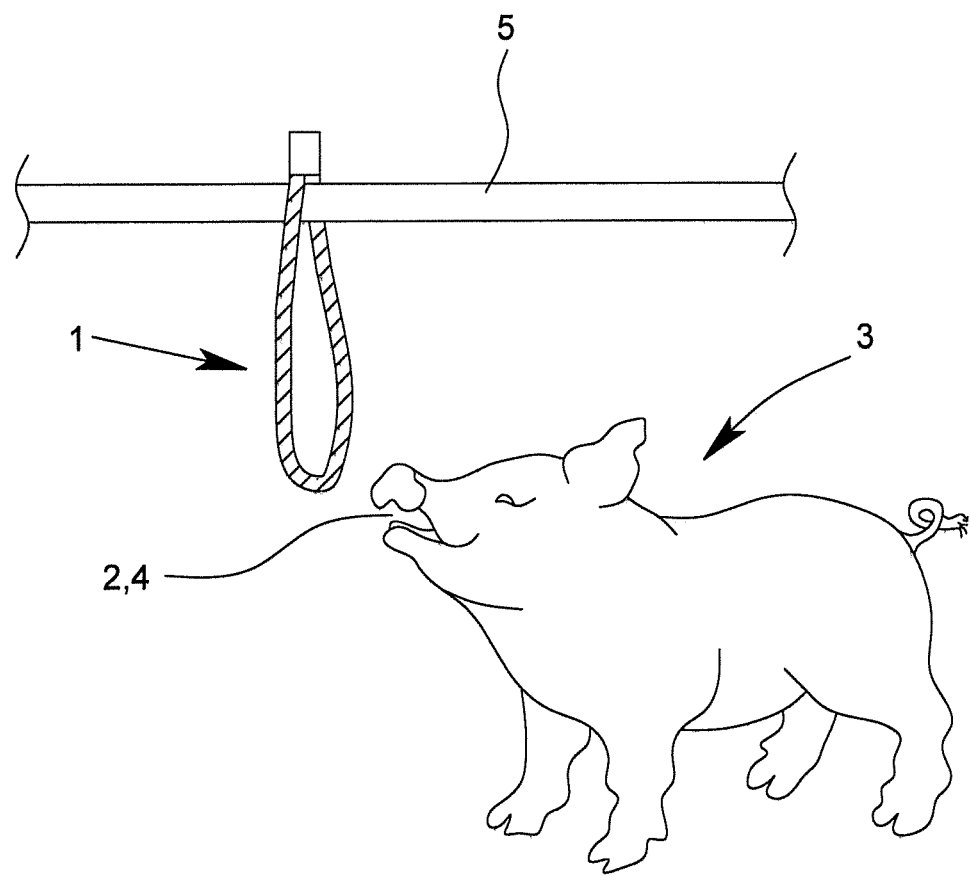
FIG. 1 is a schematic view of the taking of a sample from an animal using a receiving device.

In the figures, which are purely schematic and not to scale, the same reference numerals have been used for identical or similar parts resulting in corresponding or comparable properties and advantages, even if there is no repetition of the related description.

FIG. 1 shows a receiving device 1 for receiving saliva 2 from an animal 3. FIG. 1 shows, by way of example, the use of the receiving device 1 on a pig. However, the receiving device 1 may also be used to take saliva from another, particularly domesticated, animal 3, such as a cow, a goat, a sheep or the like.

The receiving device 1 is preferably at least substantially elongate in the shape of a rod, or ball. Particularly preferably, the receiving device 1 is at least partially in the form of a rope or cord, as shown in FIG. 1, in particular. However, other solutions or embodiments are also possible. In particular, the receiving device 1 may be at least substantially spherical, annular or cylindrical or at least partially in the form of a ball, ring or cylinder.

Preferably, the receiving device 1 is shorter than 3 m or 2 m, particularly preferably shorter than 1.5 m or 1.2 m, particularly shorter than 100 cm or 80 cm, and/or longer than 20 cm or 30 cm, particularly preferably longer than 50 cm or 60 cm.

By the term "rope" is preferably meant, according to the present invention, an elongate object which is embodied particularly for transmitting tensile forces. According to this meaning, a rope is, in particular, at least substantially axially rigid, flexible and/or elastic. Preferably, a rope is a plaited, woven or knitted structure, particularly made from fibers, or particularly preferably comprises such a structure as its casing.

Preferably, the receiving device 1 is at least substantially flexible, elastic, tear-resistant and/or bite-proof. Particularly preferably, the receiving device 1 is configured to be at least partially and/or temporarily received, chewed and/or bitten in the mouth 4 of the animal 3.

The receiving device 1 is preferably adapted to be attached, particularly suspended, in a stall (not shown). In the embodiment shown the receiving device 1 is attached to or suspended from a carrier 5. However, it is also possible to make the receiving device 1 accessible to the animal 3 in some other way.

Particularly preferably, a loop may be formed or shaped from the receiving device 1. This enables the receiving device 1 to be mounted particularly easily, quickly and/or securely.

The receiving device 1 is preferably configured to take up or absorb saliva 2, preferably by oral contact with the animal 3.

Preferably, the receiving device 1 comprises natural fibers such as cotton, linen, hemp, coconut and/or sisal, and/or synthetic fibers such as polyester, polyamide, polypropylene and/or polyethylene, and/or the receiving device 1 may be formed thereby.

Preferably, the receiving device 1 is biodegradable and/or digestible or can be broken down by digestive enzymes. This removes or reduces potential damage to the health of the animal 3 and/or ensures that the receiving device 1 or constituents of the receiving device 1 is or are tolerated by the animal 3, in the event that the animal 3 eats the receiving device 1 or parts of the receiving device 1.

Figure 2:
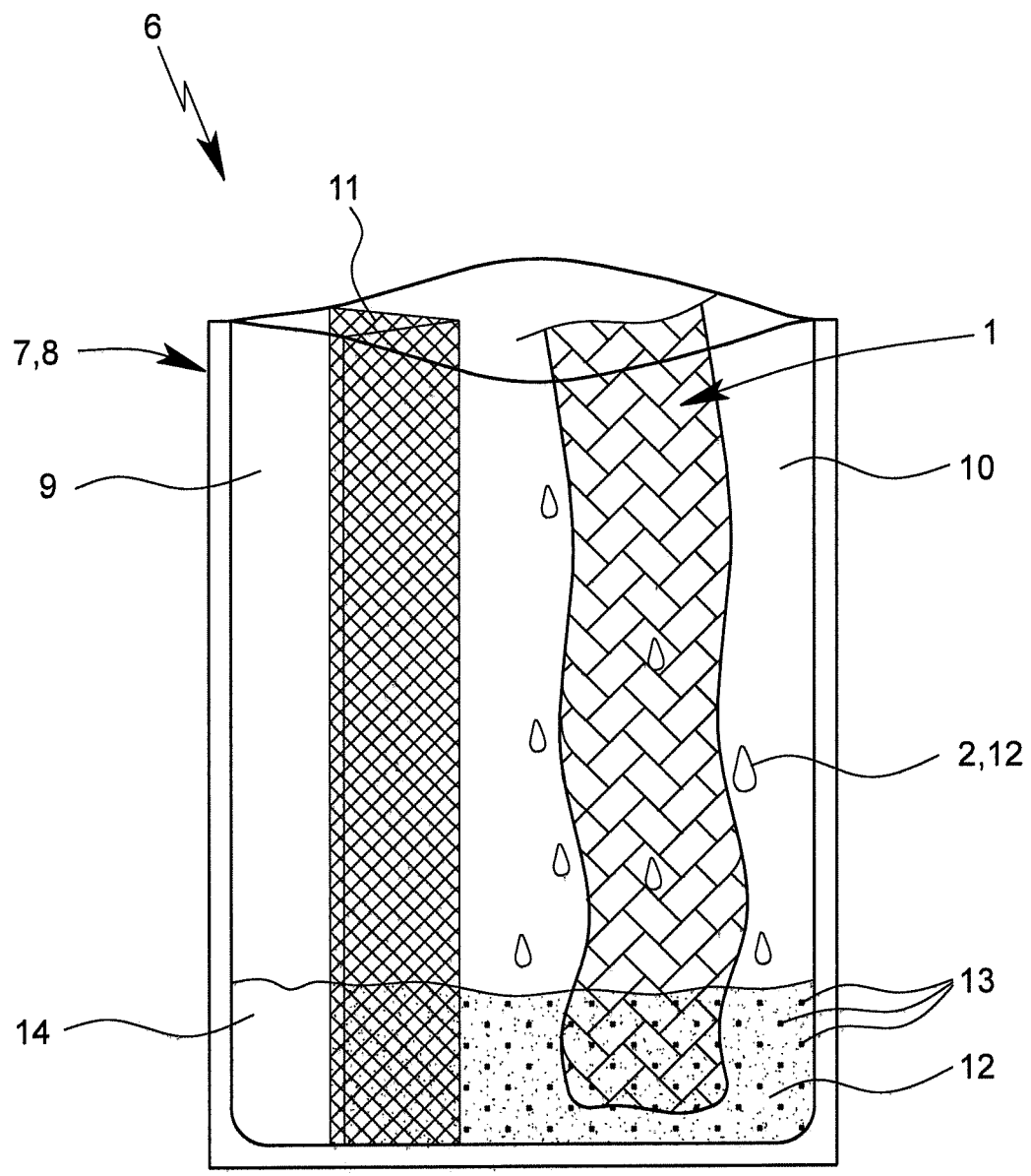
FIG. 2 is a schematic view of a proposed collecting device according to a first embodiment.

FIG. 2 shows a proposed kit 6 having the proposed receiving device 1 and a proposed collecting device 7 according to a first embodiment.

Optionally, the kit 6 contains at least a pair of gloves, instructions for use, a pipette and/or an extraction agent or solvent.

The collecting device 7 is preferably designed to at least partially accommodate the receiving device 1. In particular, the receiving device 1 can be placed in the collecting device 7.

Preferably, the collecting device 7 comprises an, in particular, flexible, elastic, pliable, deformable and/or compressible bag 8 and/or the collecting device 7 is configured as an, in particular, flexible, elastic, pliable, deformable and/or compressible bag 8.

Preferably, the collecting device 7 or the bag 8 is flexible, elastic, deformable and/or compressible, so that the receiving device 1 can be wrung out, squeezed out and/or pressed out in the collecting device 7 or in the bag 8, particularly manually. In particular, the receiving device 1 can be wrung out, squeezed out and/or pressed out by compressing the collecting device 7 or the bag 8.

In the first embodiment shown, the collecting device 7 or the bag 8 comprises a first section 9 and a second section 10, the first section 9 preferably being fluidically connected to the second section 10 through a filter 11.

Preferably, the filter 11 forms a dividing or intermediate wall in the collecting device 7 or the bag 8. In particular, the filter 11 subdivides the collecting device 7 or the bag 8 into the two sections 9 and 10 and/or the filter 11 separates the first section 9 from the second section 10.

Preferably, the first section 9 or the volume of the first section 9 is smaller than the second section 10 or the volume of the second section 10.

Preferably, the volume of the first section 9 is less than 50%, particularly preferably less than 40 or 30%, more particularly less than 20 or 10%, of the total volume of the collecting device 7 or the bag 8.

Preferably, the volume of the first section 9 and/or of the second section 10 is more than 10 ml or 30 ml, particularly preferably more than 50 ml or 100 ml, particularly more than 200 ml or 500 ml, and/or less than 5000 ml or 4000 ml, particularly preferably less than 3500 ml or 3000 ml, particularly less than 2000 ml or 1000 ml.

Preferably, the collecting device 7 or the bag 8, particularly the second section 10, is of such a size and dimensions that the receiving device 1 can be—at least partially—accommodated in the collecting device 7 or in the bag 8, particularly the second section 10.

The filter 11 is preferably in the form of a membrane, a film, a mesh or a lattice. In particular, the filter 11 is in the form of a sieve, a paper filter or a nonwoven/fleece filter.

Particularly preferably, the filter 11 is made of plastics or metal.

In particular, the filter 11 is at least substantially flexible, pliable, elastic, foldable, compressible and/or deformable. Most preferably, the filter 11 can be deformed together with the bag 8.

In the first embodiment of the collecting device 7 shown in FIG. 2, the filter 11 extends substantially over the entire height of the collecting device 7 or the bag 8. In particular, the filter 11—in the usual position of use—is substantially vertically aligned or arranged in the collecting device 7. Particularly preferably, the filter 11 subdivides the collecting device 7—in the conventional position of use—at least substantially vertically into sections 9 and 10. However, other solutions are also possible, particularly wherein the filter 11 extends over the width of the collecting device 7 or the bag 8 and/or the filter 11—in the usual position of use—is aligned or arranged substantially horizontally in the collecting device 7. In particular, the filter 11 may subdivide the collecting device 7—in the normal position of use—at least substantially horizontally into the sections 9 and 10.

The collecting device 7 is preferably configured to filter or purify saliva 2 or sample material 12 collected by the receiving device 1 by means of the filter 11. In particular, particles or contaminants 13 can be separated out of the saliva 2 or the sample material 12 by means of the filter 11.

The filter 11 preferably has a filter porosity of less than 1000 μm, particularly preferably less than 800 μm or 500 μm, particularly less than 300 μm or 100 mm. Preferably, particles or contaminants 13 measuring more than 2000 μm or 1500 μm in size or diameter, particularly preferably more than 1000 μm or 800 μm, most preferably more than 500 μm or 200 μm, particularly more than 100 μm or 50 μm, can be separated from the saliva 2 or sample material 12 by means of the filter 11.

Particularly preferably, the first section 9 is designed to collect the filtered saliva 2 or the filtered sample material 12. In particular, the collecting device 7, preferably the first section 9, is designed to prepare/provide a saliva sample 14.

Preferably, the filtered sample material 12 or the saliva sample 14 can be removed from the collecting device 7, particularly from the first section 9, by means of a syringe, pipette 18, or the like.

Figure 3:
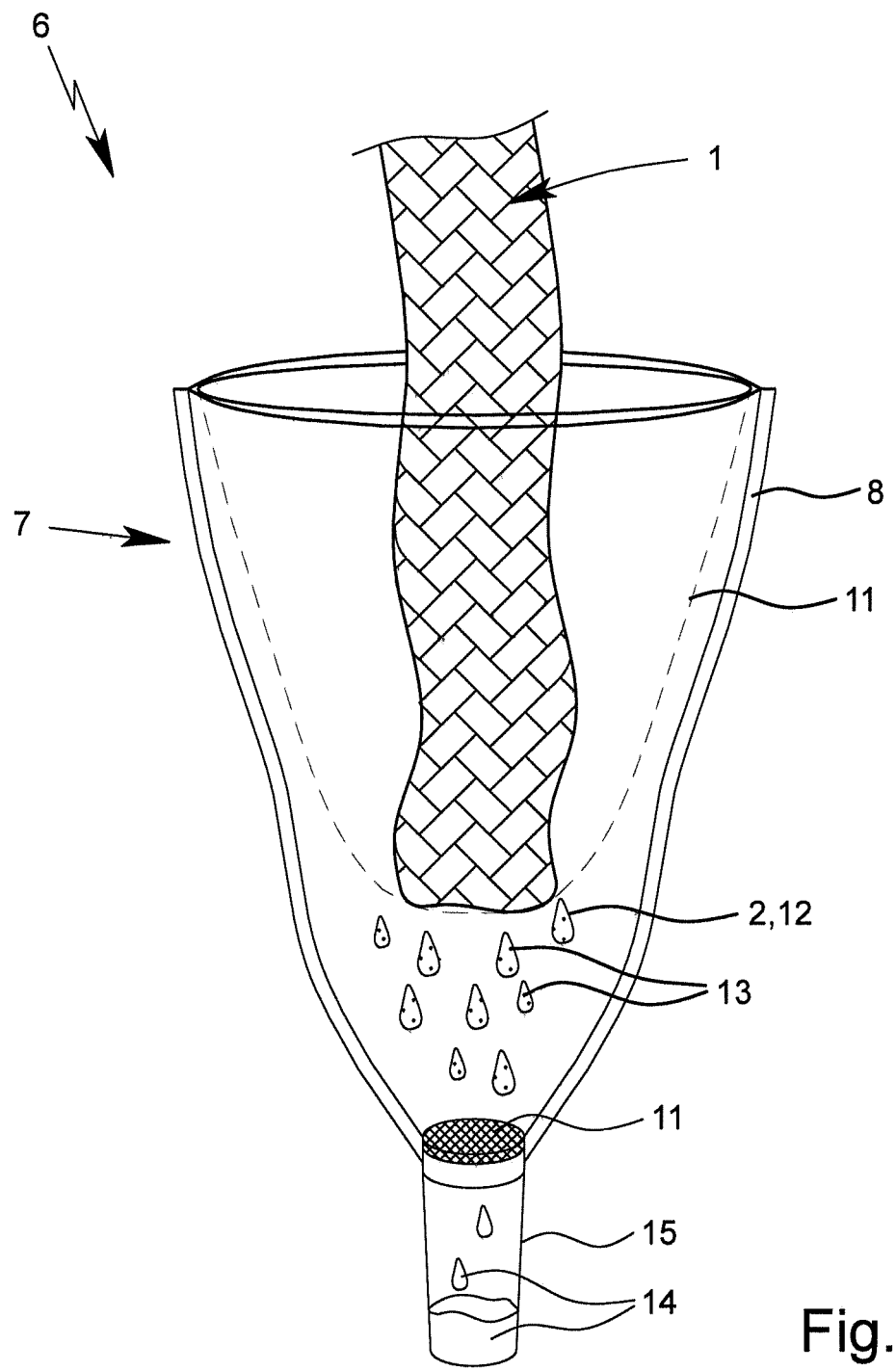
FIG. 3 is a schematic view of a proposed collecting device according to a second embodiment.
Figure 4:
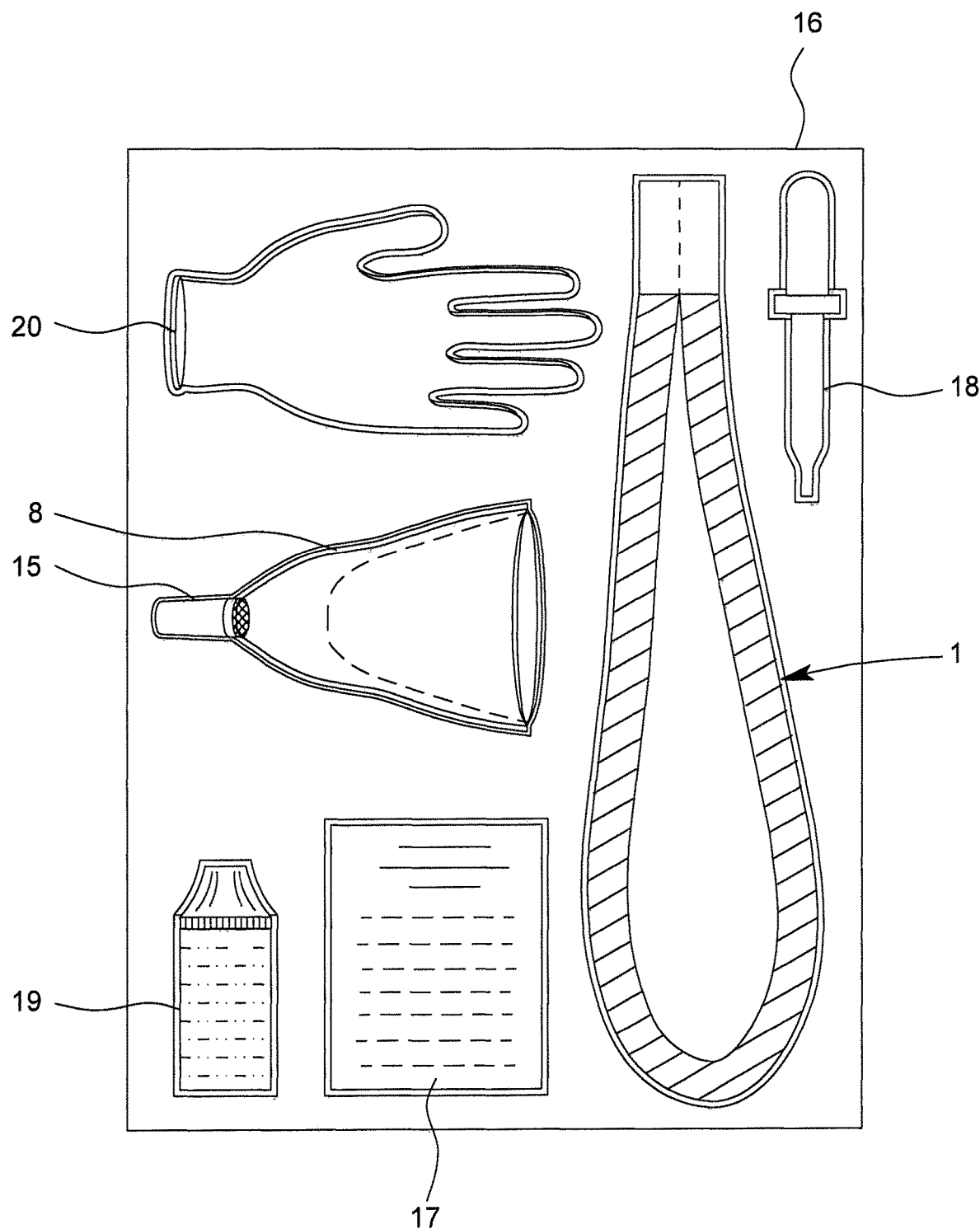
FIG. 4 shows a kit in accordance with the invention.

In the second embodiment shown in FIG. 3, the collecting device 7 or the bag 8 is at least partially embodied as a funnel or is at least partially funnel-shaped.

Preferably, the collecting device 7 comprises an optional container 15, the container 15 being at least substantially rigid in construction. Particularly preferably, the container 15 is embodied as a glass container, particularly a test tube.

The container 15 is preferably connected to the bag 8 by interlocking, frictional and/or material connection, particularly by adhesive bonding, particularly at the base or on a side of the bag 8 opposite the opening of the bag 8.

Preferably, the container 15 can be separated or removed from the bag 8, or vice versa.

The container 15 is preferably fluidically connected to the bag 8 via the filter 11. In the second embodiment shown, the container 15 preferably forms the first section 9 and the bag 8 forms the second section 10. However, it is also possible for the bag 8 to comprise or form both the first section 9 and the second section 10, the container 15 being fluidically connected, in particular, to one of the sections 9 or 10, particularly the first section 9.

Preferably, the filter 11 or an additional filter 11 may be arranged in the bag 8 or may subdivide the bag 8 into the sections 9 and 10, as indicated by dashed lines in FIG. 3. Particularly preferably, a filter or the filter 11 is—additionally or alternatively—set into, suspended or arranged in the collecting device 7 or the bag 8, in the shape of a funnel or bowl, in particular.

Preferably, the filter 11 is integrated in the collecting device 7, particularly the bag 8 and/or the container 15, and/or is fixedly attached to the collecting device 7, particularly the bag 8 and/or the container 15, particularly by interlocking, frictional and/or material connection. Particularly preferably, the filter 11 is formed by the collecting device 7, particularly the bag 8 and/or the container 15.

In the second embodiment shown in FIG. 3, the filter 11 is integrated in the opening of the container 15, or the filter 11 forms the opening of the container 15. In particular, the container 15 can be removed or separated from the bag 8 together with the filter 11. However, other solutions are also possible, in particular by having the filter 11 formed by the bag 8.

Preferably, the container 15 is configured to be sealable. This facilitates the transporting or handling of the saliva sample 14 collected in the container 15, and/or prevents the saliva sample 14 from escaping from the container 15.

The proposed method and the proposed use for obtaining an, in particular, filtered saliva sample 14 from the animal 3 will be explained in more detail hereinafter.

The proposed method or the proposed method of use is preferably carried out using the receiving device 1 or the kit 16. The proposed kit for obtaining a filtered saliva sample from an animal, particularly a pig, preferably comprises the receiving device 1, and a collecting device, formed by container 15. The kit optionally contains instructions for use 17, a pipette 18 and/or a solvent 19 for dissolving the saliva or sample material out of the receiving device. This results in corresponding advantages.

Preferably, the receiving device 1 is made available to the animal 3, particularly by allowing preferably oral contact between the animal 3 and the receiving device 1.

Preferably, the receiving device 1 is secured in a stall (not shown) by interlocking, frictional and/or material connection, preferably to the carrier 5. Most preferably, the receiving device 1 is arranged or mounted in a suspended position in a stall, as shown in FIG. 1, in particular.

Preferably, saliva 2 from the animal 3 is taken up or absorbed by the receiving device 1, particularly as a result of, in particular, oral contact with the animal 3, particularly by chewing and/or biting of the receiving device 1.

Preferably, the saliva 2 taken up or absorbed or the sample material 12 taken from the animal 3 penetrates or flows partially or completely through the receiving device 1.

The sample material 12 preferably comprises the saliva 2 as well as contaminants or particles 13. In particular, the receiving device 1 takes up or absorbs both saliva 2 and also particles or contaminants 13.

In addition, the receiving device 1 may be further contaminated or absorb further particles or contaminants 13, for example by handling in the stall.

Preferably, the receiving device 1 is released from the carrier 5 after the sampling process.

Preferably, the receiving device 1 is then at least partially placed in the collecting device 7 or the bag 8, particularly the second section 10 of the bag 8, and/or accommodated within the collecting device 7 or the bag 8, particularly the second section 10 of the bag 8.

Optionally, extraction agents or solvents are introduced into the collecting device 7 or the bag 8, for eluting or dissolving out the saliva 2 absorbed or sample material 12 by the receiving device 1.

Preferably, the receiving device 1 is wrung out, squeezed out, spun out and/or pressed out in the collecting device 7 or in the bag 8, particularly manually, so that the collected saliva 2 or the sample material 12 is at least partially released from the receiving device 1 and/or collects in the collecting device 7, particularly in the bag 8 and/or the container 15. Additionally or alternatively, the collected saliva 2 or the sample material 12 is eluted or dissolved out, preferably using a solvent.

Preferably, the collecting device 7 and/or the bag 8 is at least partially deformed or compressed, particularly in order to release the saliva 2 or the sample material 12 at least partially from the receiving device 1 or to wring out, squeeze out and/or press out the receiving device 1 in the collecting device 7 or bag 8.

Optionally, the collecting device 7 or the bag 8 can be sealed/closed, or the collecting device 7 or the bag 8 is sealed/closed, particularly in order to prevent the saliva 2 or saliva sample 14 from escaping.

Preferably, the saliva 2 or the sample material 12 is at least partially filtered in the collecting device 7, particularly by means of the filter 11, at least substantially at the same time as the saliva 2 or sample material 12 is separated from or dissolved out of the receiving device 1.

Preferably, the saliva 2 or the sample material 12 in the collecting device 7 which has been separated from or dissolved out of the receiving device 1 flows from the second section 10 into the first section 9 and/or through the filter 11 and/or from the bag 8 into the container 15. In particular, the sample material 12 or the saliva 2 is—at least substantially automatically—filtered in the collecting device 7 or through the collecting device 7.

Preferably, at least larger or coarser particles 13 in the saliva 2 are filtered or deposited on the surface of the filter 11 and/or in the filter 11, particularly such that filtered or purified saliva 2 flows into the first section 9 and/or into the container 15 and/or the purified saliva sample 14 can be removed from the first section 9 or the container 15.

Preferably, the container 15 is separated from the collecting device 7 or the bag 8, particularly pulled off or twisted off. The container 15 may be sealed/closed for better handling or transporting.

Preferably, the saliva sample 14 thus obtained and/or the container 15 containing the saliva sample 14 is then taken for immediate or direct veterinary examination, particularly on the spot or close to the sampling site and/or in a location remote from a laboratory, preferably with no need for any further processing or filtering of the saliva sample 14.

However, the saliva sample 14 may also be removed directly from the collecting device 7, particularly the container 15 and/or the first section 9, preferably using a syringe, pipette or the like.

Preferably, the filtered sample material 12 or the saliva sample 14 is examined, particularly directly or immediately, preferably for diseases and/or pathogens, particularly microorganisms and/or antibodies.

Preferably, the filtered sample material 12 or the saliva sample 14 has a volume of more than 1 ml or 2 ml, particularly preferably more than 5 ml or 8 ml, particularly more than 10 ml or 15 ml.

Individual aspects and features of the proposed invention or embodiments may be implemented independently of one another, but also in any desired combination or sequence.

What is claimed is:

1. A method for obtaining a saliva sample from an animal, comprising:
   using a receiving device to absorb saliva from the animal;
   at least partially accommodating the receiving device in an at least partially flexible bag of a collecting device;
   separating the saliva absorbed by the receiving device from the receiving device in the collecting device at least in part by squeezing of the at least partially flexible bag,
   at least partially filtering the saliva by means of a filter of the collecting device to obtain a saliva sample,
   wherein the filter forms a dividing wall in the at least partially flexible bag which subdivides the at least partially flexible bag into two sections separated by the filter, one section of the two sections being configured to receive the receiving device with the saliva sample in unfiltered form and the other section of the two sections being configured to collect the saliva sample in filtered form after having passed through the filter.

2. The method according to claim 1, wherein the saliva sample is collected in least one removable container that is fluidically connected to the at least partially flexible bag of the collecting device via a second filter.

3. The method according to claim 1, wherein the saliva from the animal is absorbed, by the receiving device by oral contact with the animal.

4. The method according to claim 1, further comprising at least partially separating the saliva from the receiving device by the saliva being dissolved or eluted by means of a solvent in the collecting device.

5. The method according to claim 1, wherein particles or contaminants are separated off by said filtering.

6. The method according to claim 1, wherein the saliva is filtered simultaneously with the separation of the saliva from the receiving device.

7. The method according to claim 1, wherein the filtered sample is at least partially removed from the collecting device by means of a syringe, a pipette or a container.

8. The method according to claim 1, wherein the saliva is filtered at a location remote from a laboratory.

9. The method according to claim 1, wherein the animal from which the saliva is collected is a pig.

* * * * *